US006328035B1

(12) United States Patent
Wakefield et al.

(10) Patent No.: US 6,328,035 B1
(45) Date of Patent: Dec. 11, 2001

(54) PNEUMATIC BREATH ACTUATED INHALER

(75) Inventors: Keith Wakefield, Clayton; Perry A. Genova, Chapel Hill, both of NC (US)

(73) Assignee: IEP Pharmaceutical Devices Inc., Raleigh, NC (US)

( * ) Notice: Subject to any disclaimer, the term of this patent is extended or adjusted under 35 U.S.C. 154(b) by 0 days.

(21) Appl. No.: 09/567,352

(22) Filed: May 9, 2000

(51) Int. Cl.[7] .................................................. A61M 15/08
(52) U.S. Cl. .............................. 128/203.23; 128/203.2; 128/200.14; 128/203.12; 128/103.15
(58) Field of Search .................... 128/203.23, 200.14, 128/200.18, 200.19, 200.21, 200.22, 203.15, 203.12

(56) References Cited

U.S. PATENT DOCUMENTS

| 3,636,949 | * | 1/1972 | Kropp ............................ 128/200.23 |
| 4,648,393 | | 3/1987 | Landis et al. . |
| 4,664,107 | | 5/1987 | Wass . |
| 4,955,371 | | 9/1990 | Zamba et al. . |
| 5,027,808 | | 7/1991 | Rich et al. . |
| 5,057,281 | | 10/1991 | Torti et al. . |
| 5,060,643 | | 10/1991 | Rich et al. . |
| 5,069,204 | | 12/1991 | Smith et al. . |
| 5,119,806 | | 6/1992 | Palson et al. . |
| 5,217,004 | | 6/1993 | Blasnik et al. . |
| 5,345,980 | | 9/1994 | Burt et al. . |
| 5,347,998 | | 9/1994 | Hodson et al. . |
| 5,388,572 | | 2/1995 | Mulhauser et al. . |
| 5,408,994 | | 4/1995 | Wass et al. . |
| 5,447,150 | | 9/1995 | Bacon . |
| 5,507,281 | | 4/1996 | Kuhnel et al. . |
| 5,515,842 | * | 5/1996 | Ramseyer et al. ............... 128/200.18 |
| 5,655,516 | | 8/1997 | Goodman et al. . |
| 5,692,492 | | 12/1997 | Bruna et al. . |
| 5,775,320 | | 7/1998 | Patton et al. . |
| 5,809,997 | | 9/1998 | Wolf . |
| 5,819,726 | | 10/1998 | Rubsamen et al. . |
| 5,826,570 | | 10/1998 | Goodman et. al. . |
| 5,826,571 | | 10/1998 | Casper et al. . |
| 5,904,139 | | 5/1999 | Hauser . |
| 6,029,662 | | 2/2000 | Marcon . |

* cited by examiner

Primary Examiner—John G. Weiss
Assistant Examiner—V. Srivastava
(74) Attorney, Agent, or Firm—Frommer Lawrence & Haug LLP

(57) ABSTRACT

A device for dispensing medication in an aerosol form from an MDI. The device is pre-loaded so as to automatically discharge the medication upon inhalation on the mouthpiece.

15 Claims, 6 Drawing Sheets

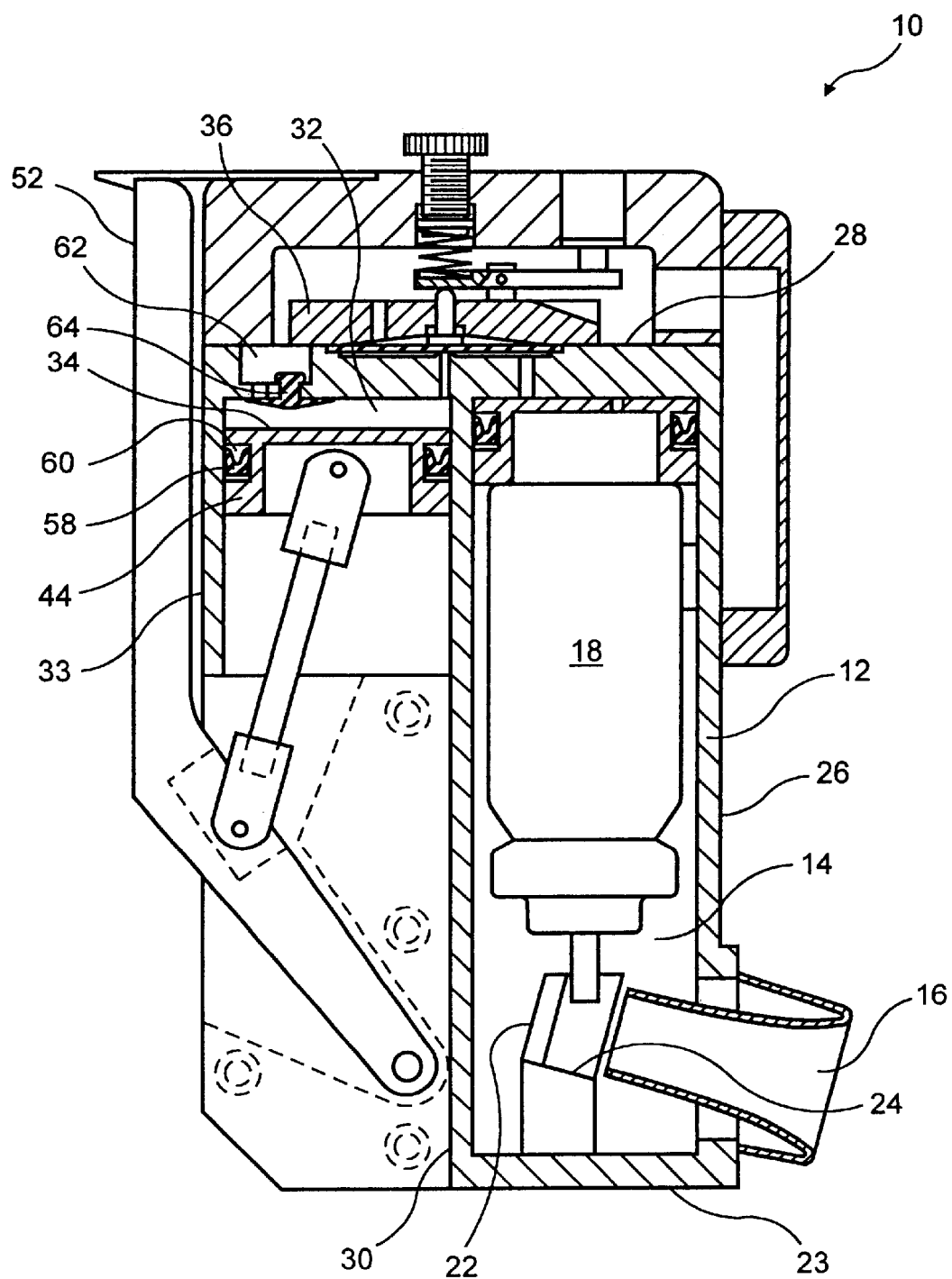
F I G. 2

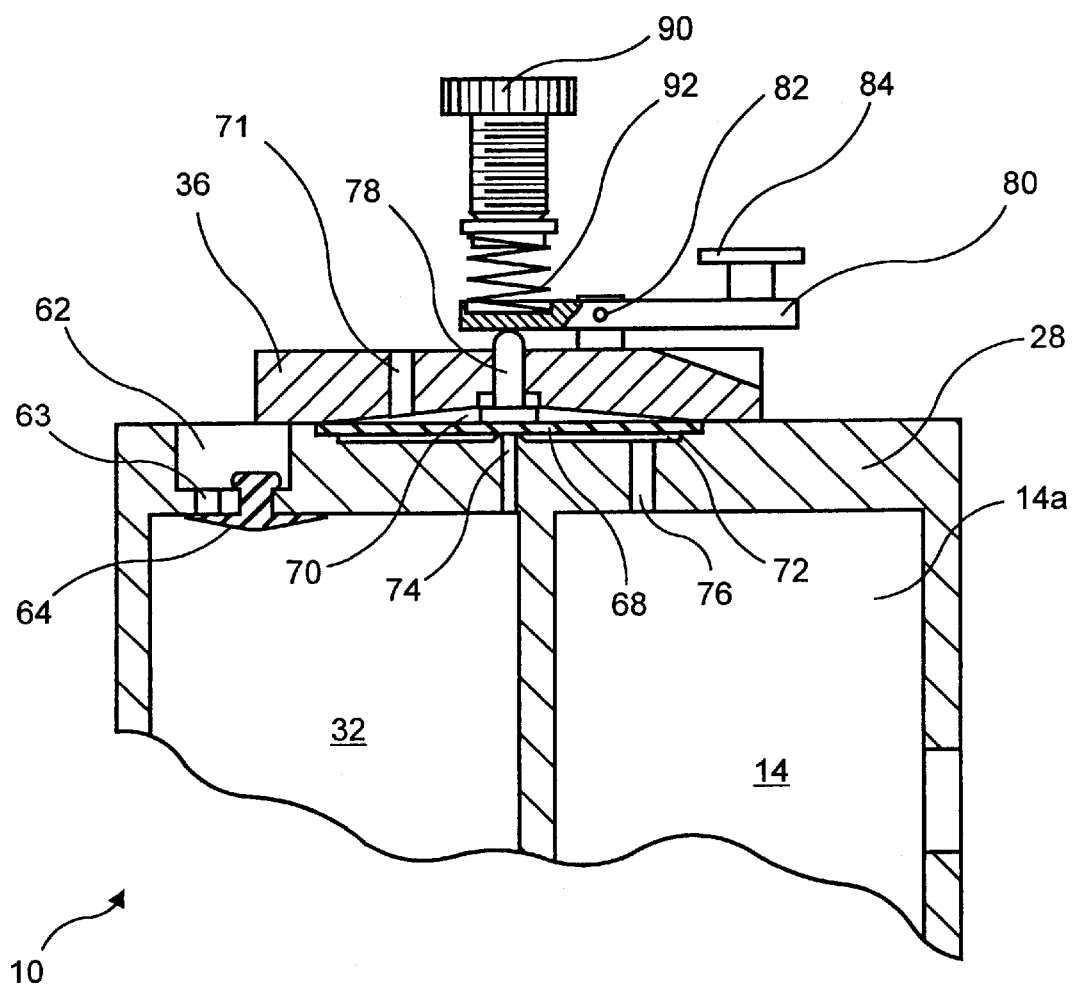
F I G. 5

PNEUMATIC BREATH ACTUATED INHALER

BACKGROUND OF THE INVENTION

1. Field of the Invention

The present invention is directed to a breath actuated pulmonary drug delivery device used in the delivery of fluid dispensations from a drug-containing canister. The delivery device provides a metered dose of drug or other therapeutic agent when the patient inhales from the device.

2. Brief Description of Related Art

There are a variety of inhalation devices which release aerosol medication, either in a continuous spray or in a predetermined amount of medication, commonly referred to as a metered dose. The spray is applied directly into the patient's mouth, nasal area or respiratory airways. Typically, these devices are actuated by the pressure applied by the user's fingers, button action, or other related manual techniques. While there are devices which are activated by the inhalation of the users, some of which are very satisfactory, as with all things, variations or improvements are desirable.

Metered dose aerosol canisters of the medicine to be inhaled into the mouth, nasal areas or respiratory airways are manufactured by a variety of pharmaceutical companies. Metered dose aerosols are much the same as non-metered aerosol except that when the valve is depressed, a continuous spray is not discharged. Instead, a predetermined measured volume is discharged as a spray, releasing a fixed amount of medication. Examples of such metered dose inhalers are disclosed in U.S. Pat. No. 5,544,647, entitled "Metered Dose Inhaler"; and U.S. Pat. No. 5,622,163 entitled "Counter for Fluid Dispensers"; and U.S. patent application Ser. No. 09/241,010 filed Feb. 1, 1999 entitled "Metered Dose Inhaler Agitator" (commonly assigned), the disclosures of which are incorporated herein by reference.

A wide variety of fluid dispensers are known and commercially available to dispense metered proportions of a contained fluid from containers. For example, U.S. Pat. No. 3,749,290 describes a trigger actuated dispensing pump assembled with a fluid container. Upon actuation, a measured proportion of the contained fluid is dispensed from the containers.

"Pumping" type inhalers are known in the art. The device may be manually pumped (such as described in U.S. Pat. No. 5,284,132) or a pumping like cycle may be utilized. The medication may also be repeatedly released from a pressurized disposable canister to create repeated sprays or inhalations as needed.

Proper use of these manually actuated devices requires that the spray be activated at the beginning of the inspiratory cycle, so that the medication is carried into the lungs rather than being deposited in the mouth or throat. If this actuation is not correctly coordinated with the inspiratory phase, the metered dose may be deposited differently with each actuation and potentially compromise the therapeutics and safety of the product. A breath actuated device helps eliminate this problem by making the product easier to coordinate and more patient friendly, with predictable delivery and dispersion in the respiratory airways.

There are numerous factors leading to poor coordination of actuation of the spray and the inspiration cycle. Included in those factors are the inherent limitations of the users (if any), such as impaired physical abilities associated of geriatric patients or the as-yet-undeveloped skills of children, or their inability of either group to comprehend the correct way to use the device. Recognizing the need for correct and accurately delivered doses in the asthmatics, COPD patients and, as with other patients with other respiratory illnesses, a reliable breath activated device would improve the quality of life for these afflicted people.

Metered dose inhalers are, at present, the most efficient and best-accepted means for accurately delivering medications in measured doses to an animal's respiratory tract. Therapeutic agents commonly delivered by the inhalation route include bronchodilators (B2 agonists and anticholinergics), corticosteroids, and anti-allergics. Inhalation may also be a viable route for anti-infective, vaccinating, systemically acting and diagnostic agents, as well as anti-leukotrienes, anti-proteases and the like.

Metered dose inhalers are available in several types. Most frequently, metered dose inhalers comprise a chamber into which a pressure resistant container (canister) is placed. The container is typically filled under super-atmospheric pressures with a product such as a drug dissolved in a liquefied propellant, or micronized particles suspended in a liquefied propellant. The container is fitted with a metering valve. The valve is movable from an inner (charging) position to an outer (discharging) position. A spring bias holds the valve in the charged position until forced to the discharge position. Actuation of the metering valve allows a metered portion of the canister content to be released, whereby the pressure of the liquefied propellant carries the dissolved or micronized drug particles out of the container and to the patient. A valve actuator also functions to direct the aerosol as a spray into the patient's oropharynx. Surfactants are usually dissolved in the aerosol formulation and can serve the dual functions of lubricating the valve and reducing aggregation of micronized particles.

Representative of pharmaceutical formulations for use in metered dose inhalers are those described in U.S. Pat. No. 5,190,029. The metered dose inhalers for administering such pharmaceutical formulations are also well known as seen for example in the descriptions given in U.S. Pat. Nos. 3,361,306; 3,565,070; and 4,955,371 which are incorporated herein by reference thereto.

SUMMARY OF THE INVENTION

It is therefore a principled object of the invention to provide for an inhaler that is economical to manufacture, extremely easy to use, and delivers a metered dose of medicine, precise from dose to dose, in response to breath actuation and more particularly, in response to inspiration.

The device of the invention is intended for use with one fluid container and is disposable with it when the contents are emptied. One need not reset a counter with the possible errors attendant with such a procedure.

The present invention is directed to a pneumatically actuated, metered dose dispenser for an aerosol medication. The device has a housing defining a body portion into which the medicine-containing a canister is retained, and a mouthpiece for insertion into a patient's mouth. A mechanical lever or other pneumatic means which operates a compressor pump is provided upon the device, and after the device is pumped with a charge of compressed gas, maintained in a second chamber, a transfer valve is tripped by the vacuum formed when the user inhales from the device. This causes the compressed gas to enter a second chamber where the drug containing canister is maintained. This effects a depression of the canister valve stem, releasing the drug in an aerosol form. The release of the drug occurs at the same time as inhalation, insuring the delivery of a metered dose of medicine to the target location. In other words, the medicine is not mistargeted to the throat and upper mouth. The device of the present invention is relatively simple to operate, even by young children (6 to 12 years of age), and older patients as well, since inhalation initiates the dispensing of the drug.

BRIEF DESCRIPTION OF THE DRAWINGS

Embodiments of the present invention will be described with reference to the accompanying drawings in which:

FIG. 2 is a cross sectional view of a preferred embodiment of the present invention showing the device in the cocked position.

FIG. 5 is a cross sectional view of a preferred embodiment of the present invention showing the transfer valve in the cocked position.

DETAILED DESCRIPTION OF THE PREFERRED EMBODIMENTS

Figure 1:
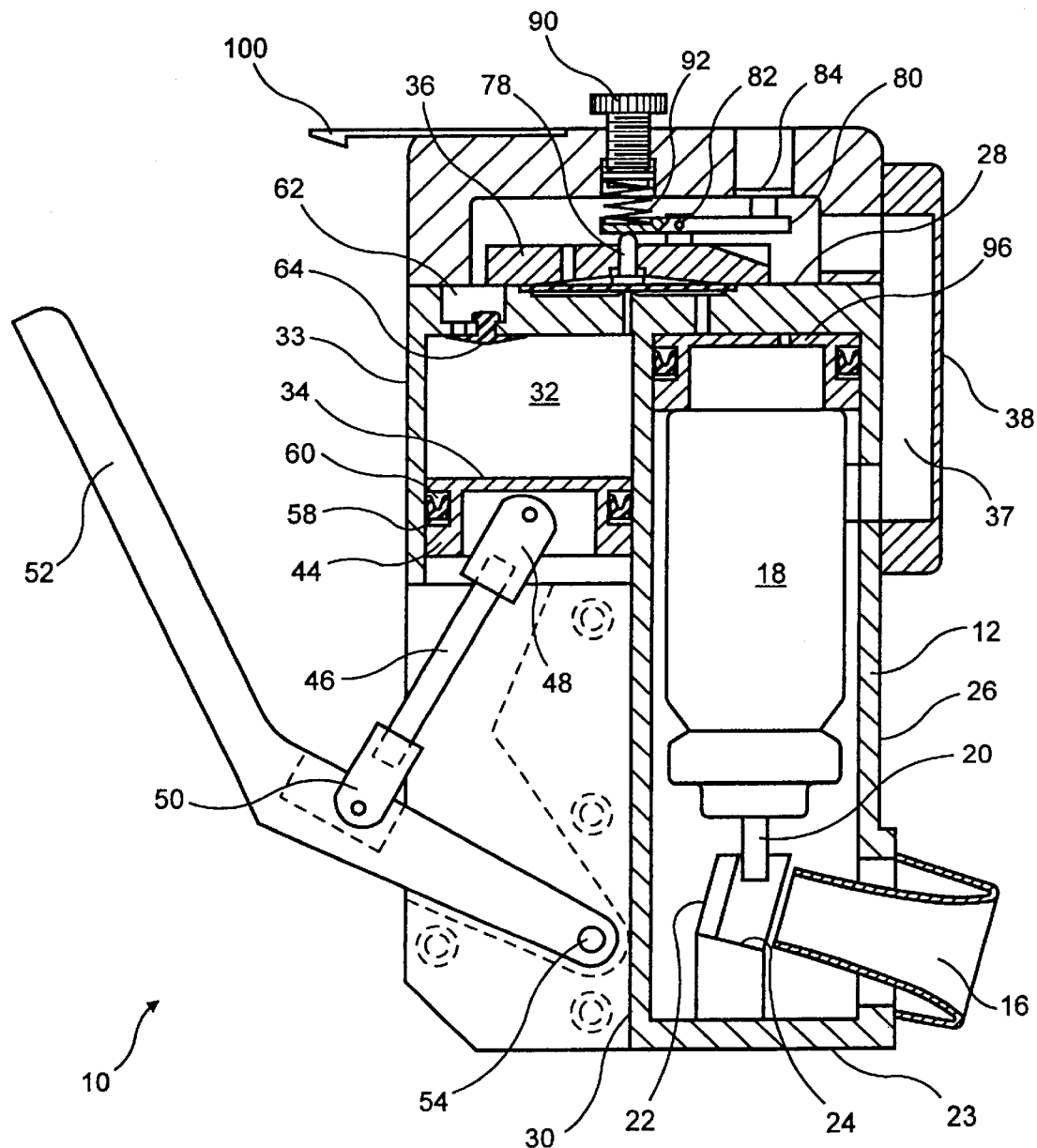
FIG. 1 is a cross sectional view of a preferred embodiment of the present invention showing the device in the at rest position.

Turning now more particularly to the drawings, in FIG. 1 there is a view showing pneumatically actuated breath inhaler device 10, which comprises a housing 12 having a chamber 14 opening at mouthpiece 16. Aerosol canister 18 is mounted within the chamber 14, with the canister valve stem 20 pointed downwardly and located inside nozzle 22 and positioned just above the impinging surface 24. This surface is shown as a relatively flat surface. When the valve stem is impinged against it, in response to displacement of the canister during the pneumatic actuation, the medicine is discharged as an aerosol. The nozzle 22 directs the spray outward into the mouthpiece 16.

The first chamber 14 is defined by lower wall 23, outer wall 26, both of the housing 12, mouth piece 16, upper surface 28 and partitioning wall 30. A second chamber 32 is formed on the other side of partitioning wall 30, defined by the partitioning wall 30, upper surface 28, and outer wall 33. A movable piston 34 provides the lower surface of the second chamber 32. The second chamber is variable with respect to the location of the piston 34 within the chamber, and in fact the piston is used to compress an initial volume of gas into a smaller one, which increases the pressure of the gas. The energy stored in the compressed gas is used to effect the discharge of the medicine from the canister. This will be explained in detail later.

There is a third chamber 37 of the device, defined by the outer wall 12, upper surface 28, transfer valve cover 36, airway cover 38, and airway frame 40.

The upper portion of the compression piston 34 is attached to piston support 42 forming compression piston assembly 44. Connecting link 46 is affixed to the compression piston assembly at first end 48. The second end 50 of the connecting link 46 is affixed to the cocking lever 52. The cocking lever 52 is pivotally mounted about axial attachment rod 54, which fixedly attaches the cocking lever 52 to the housing. The cocking lever pivots between an charging position C and a firing position F, which will be explained later.

The compression piston 34 is a cylinder that is dimensioned to fit snugly against the inner walls of the second chamber 32 and is formed a solid, non impervious material, so that when the piston is moved into the cocked position, the fluid within the second chamber is compressed. The piston is provided with U-cup seals 58 which are situated within openings 60 in the piston assembly 44. In the place of the piston seals, such a rolling diaphragm seal, or a bellows-type system can also be used. The connecting link 46 could also be replaced by several links configured to toggle, negating the need for a latch.

The upper surface 28 in the second chamber 32 has an aperture 62 into which an elastomeric umbrella check valve 64 is fitted. When the pump lever is moved away from the body of the device, the connecting link 46 pulls the compression piston 34 downward. This action draws ambient air past the umbrella check valve 64 through passage 63 and into the second chamber 32.

A transfer valve cover 36 is located upon the upper surface 28 which defines the first and second cavities 14 and 32. As is more clearly shown in FIG. 2, the transfer valve 36 cover contains an elastomeric diaphragm 68 that is provided in a fluid pathway 70 between the transfer valve cover 36 and the upper surface 28 of the housing. The elastomeric diaphragm 68 is clamped at its periphery between the transfer valve cover 36 and the upper surface 28 of the housing to form an air tight seal. There is a shallow chamber 72 beneath the diaphragm with an orifice 74. When the pathway 70 is open, the pathway 70 and second chamber 32 are in fluid communication with each other. Also provided is a transfer port 76, which is an orifice that is in fluid communication with chamber 14a which is a subchamber of chamber 14 and is positioned between surface 28 and actuation piston 96 and is formed by the movement thereof (see FIG. 3). When the pathway 70 is open, the pathway 70 and chamber 14a are in fluid communication with each other, and the compressed fluid can flow from the second chamber to the chamber 14a.

Figure 3:
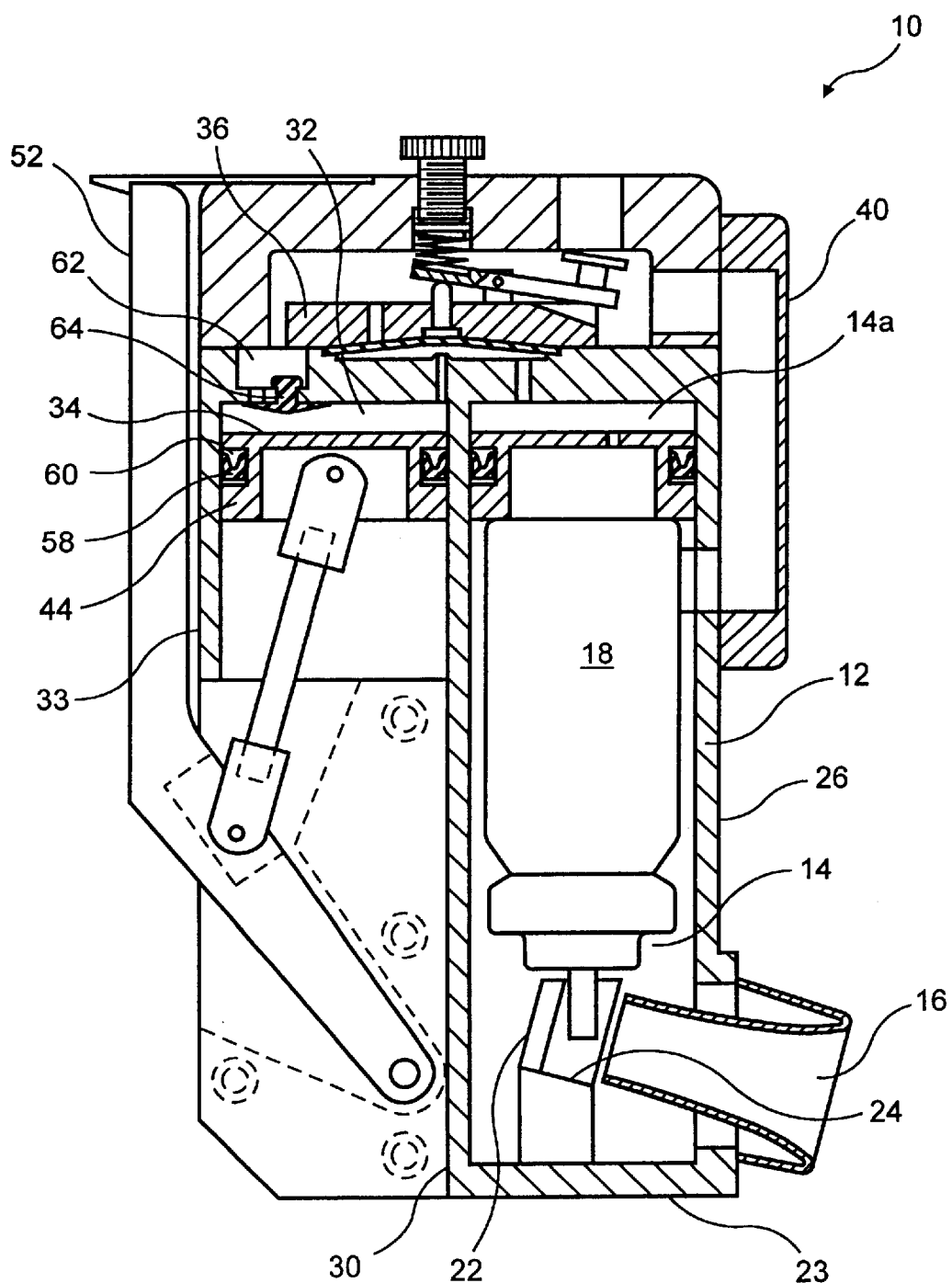
FIG. 3 is a cross sectional view of a preferred embodiment of the present invention showing the device in the fired position.
Figure 4:
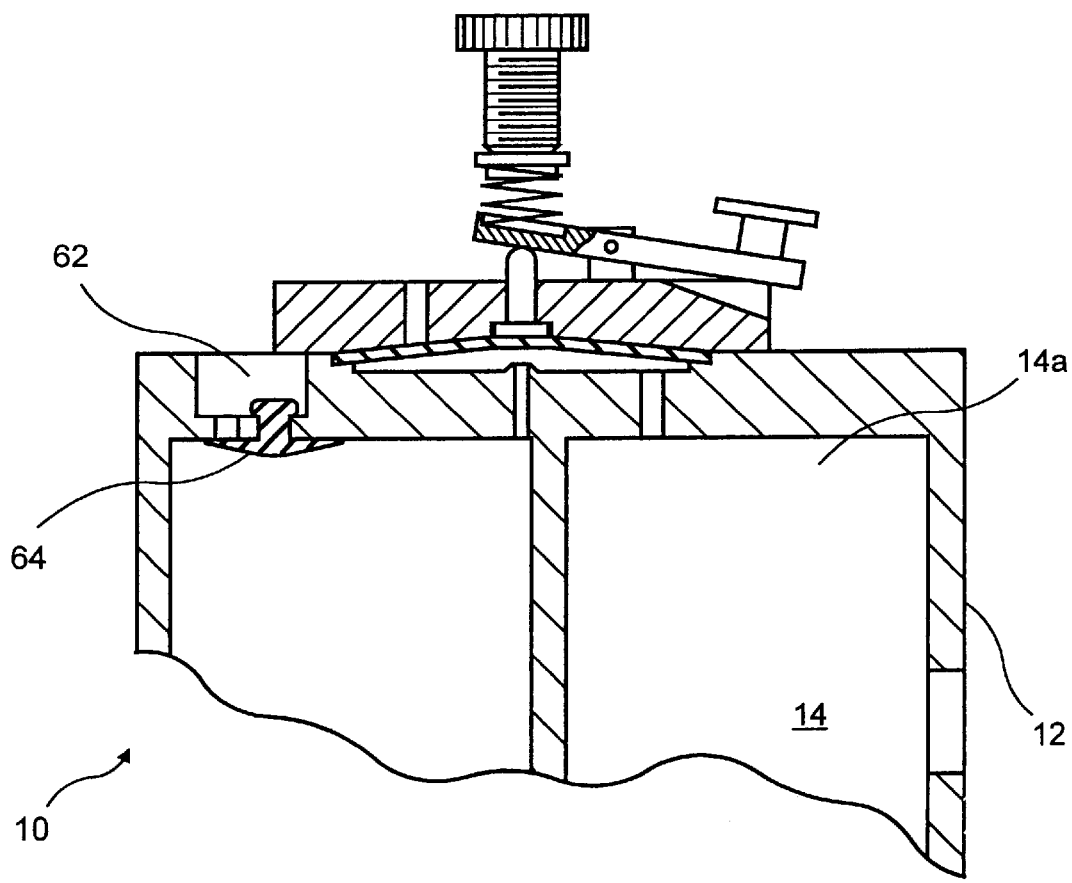
FIG. 4 is a cross sectional view of a preferred embodiment of the present invention showing the transfer valve in the fired position.

Above the diaphragm 68 there is a pin 78 that passes through the transfer valve cover 66 and presses against the diaphragm 68, providing a counterforce against the compressed fluid in the second chamber 32, insuring that the diaphragm is sealed. At its top, the pin 78 is maintained in place by the airway door support 80, mounted about pivot 82. At its right hand end, the airway door support 80 provided with airway door 84, shown as resembling a nail and its head, wherein the head is dimensioned to fit into and seal an aperture 86, as shown in FIGS. 1, 2, and 3. On its left-hand side, airway door support 80 is provided with a groove or receptacle 94 for receiving biasing spring 92. Above the receptacle 94, airway frame 40 is provided with a threaded aperture 88 into which an adjustable screw 90 is fitted. The biasing spring 92 is connected to. the adjustable screw 90 at one end and at the other end is positioned in the groove or receptacle 94 on the airway door support 80. Screw 90 provides for a tensioning of the spring 92 to a desired level. Of course, the screw 90 can be eliminated, with an appropriately pretensioned spring utilized, thereby substituting for the screw 90, spring 92 combination. Other means suitable for purpose may also be utilized in this regard.

The tension provided by the spring causes the airway door to press downwardly on the diaphragm 68, thereby effecting a seal which will maintain the pressurized fluid in the second chamber until the device is actuated.

A transfer valve cover 36 is located upon the upper surface 28 which defines the first and second cavities 14 and 32. The transfer valve cover 36 contains the charge of compressed air in the second chamber 32 until the user inhales from the device. When sufficient vacuum is created in the device, the transfer valve snaps open and allows pressure to transfer from the second chamber 32, to the first chamber 14a.

Turning back to the first chamber 14, an opening is provided in the housing wall 12 so that first chamber 14 is in fluid communication with third chamber 37. The third chamber is also in fluid communication with the mouthpiece as well. An actuation piston 96 is provided with U-cup seals 98 that abut against the canister 18, at the lower end of the piston 96, and a lower part of the upper surface 28. There is little, if any, open volume in the space between the lower part of the upper surface 28 and the actuation piston 96. The actuation piston 96 fits snugly against the housing wall 12 and the partition wall 30, in order to form a seal that prevent leakage of the compressed gas when it is released from the second chamber. Note that the actuation piston (and for that matter the compression piston) may take on a variety of forms including rolling diaphragms, bellows, etc. or other means suitable for purpose The valve cover 36 is provided with vent orifice 71 which exposes the upper portion of the space to the ambient atmosphere in the first and third chambers 14 and 37.

The preferred embodiment described above is operated in the following manner. After a canister has been loaded into the first chamber, the user moves the cocking lever 52 away from the device and then moves it inwards towards the housing. When the cocking lever is moved away from the body of the device, the connecting link 46 pulls the compression piston 34 downward. This action draws ambient air past the umbrella check valve 64 through passage 63 and into the compression cylinder. The cocking lever 52 is then moved back to its original position adjacent to the body of the device, forcing the compression piston upward, thereby reducing the volume in the chamber and compressing the fluid in the chamber. A latch 100 provided in the airway frame 40 latches to the top end of the cocking lever 52 and restrains it while the piston is compressing the fluid.

When the user inhales through the mouthpiece 16, creating vacuum inside the device (specifically, in the first and third chambers 14 and 37, and in the upper space of the fluid pathway 70 through vent orifice 71), the differential pressure across the diaphragm 68 increases rapidly, instantaneously exceeding a threshold value at which the biasing spring 92 can no longer keep the diaphragm in the sealed position. The diaphragm 68 snaps open and the compressed fluid exits the second chamber 32, traverses the fluid pathway 70, and enters the first chamber 14 through transfer port 76, applying pressure to the actuation piston 96. The force acting on the actuation piston 96 overcomes the return spring in the canister valve 20, moving the canister and/or valve the cause the dispensation of the medicine as an aerosol. The medicine is dispensed through the nozzle 22 and mouthpiece 16. As the diaphragm 68 snaps open, the airway door 84, contemporaneously opens (see FIG. 5) which allows the user to suck air therethrough while the medication is being dispensed. A bleed orifice 102 in the crown of the actuation piston 96 slowly bleeds off the compressed air contained between the upper surface 28 and the piston 96, permitting the canister return spring (not shown) to push the piston back to its original position, without user intervention. This prevents canister leakage that can occur if the valve stem remains depressed for prolonged periods. Moreover, as the pressure equalizes throughout the interior of the device, the biasing spring 92 returns the diaphragm 68 to the sealed position.

It should be evident to the skilled artisan that inhalation and discharge of the medicine from the container are very quick on the order of about 200 milliseconds, which insures that the inhalation of the medicine commences at the beginning of the inhalation, insuring delivery of the drug to a greater degree of targeted surface area, which ordinarily is the lungs, than is usually possible.

Figure 6:
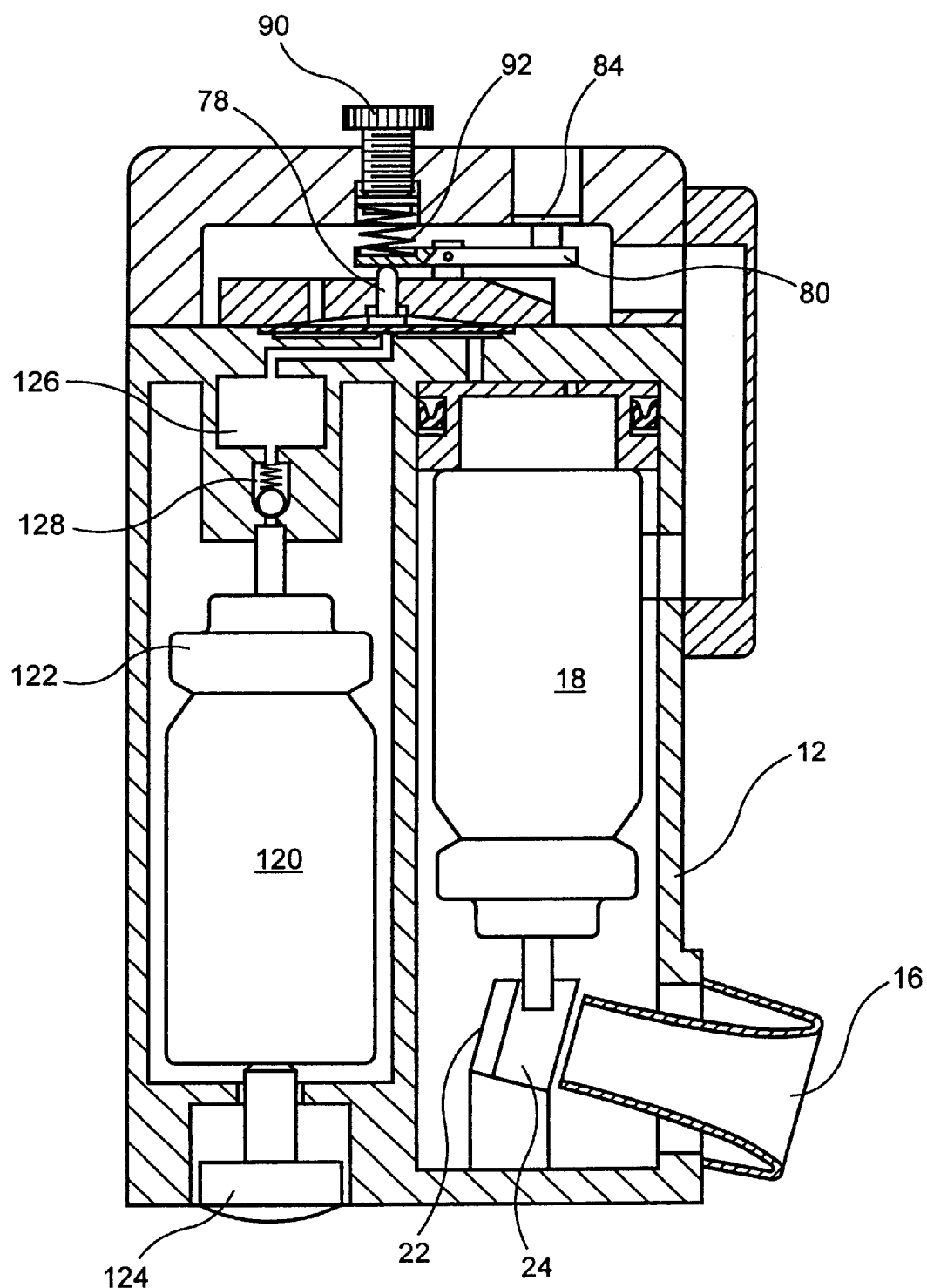
FIG. 6 is a cross sectional view of an alternative preferred embodiment of the present invention.

Turning now with regard to FIG. 6, an alternate embodiment of the present invention is shown with like parts similarly numbered. The main difference between this embodiment and the one earlier described is that the hand-powered pump is replaced by a canister 120 of liquefied propellant gas. Certain additional benefits include reduced complexity and cost, reduced cocking force, and reduced device size.

The propellant canister 120, like the medication canister 18, contains an integral metering valve 122 that dispenses a precise volume of propellant liquid when a valve stem is depressed. Rather than moving a cocking lever, depressing the propellant canister near button 124 and, in turn, metering valve 122 prepares the device for firing. The propellant metering valve 122 should be capable of delivering liquid when actuated in any orientation.

After being dispenses from the metering valve 122, the propellant is contained in a pre-chamber 126, where any remaining liquid quickly flashes to vapor and pressure stabilizes at a level above atmospheric, but below that in the canister. A check valve 128 incorporated into either the canister metering valve or the device body seals the pre-chamber inlet. The transfer valve cover 36 seals the pre-chamber outlet until the user triggers the device. When the-device is triggered, the propellant vapor actuates the drug canister in the same manner as the hand-powered version.

The objects and advantages of the present invention are realized in accordance with the disclosure set forth above. Although preferred embodiments have been described in detail, the scope of the present invention should not be limited by this disclosure, but rather its scope should be determined by the appended claims.

We claim:

1. A drug dispensing device actuated when a patient inhales from the device, comprised of:

(a) a first chamber for retaining a medication containing canister, the first chamber being in fluid communication with a mouth piece through which a patient inhales a metered dose of a medication dispensed as an aerosol, the first chamber including an actuable means positioned within the first chamber between the canister and first chamber entry means in fluid communication with an openable and closeable first fluid pathway;

(b) a second chamber including a compression means in communication with the second chamber to provide compression therein, the second chamber further including outlet means in fluid communication with the openable and closeable first fluid pathway;

(c) means for sealing the first fluid pathway in a closed position; and (d) biasing means for maintaining the seal means in a closed position and for opening the seal means when the differential pressure across the diaphragm exceeds a threshold value, the biasing means being located in a second fluid pathway in fluid communication with the mouthpiece.

2. The device of claim 1 wherein the first chamber is provided with a nozzle having a surface positioned to impinge against a valve stem of the canister in response to the displacement of the canister or displacement of the valve stem.

3. The device of claim 1 wherein the second chamber is provided with an aperture for drawing a fluid into the chamber.

4. The device of claim 3 wherein the aperture is provided with means to seal the second chamber actuable when a fluid is compressed within the chamber.

5. The device of claim 1 further comprised of an opening between the second fluid pathway and the first chamber.

6. The device of claim 1 wherein the first fluid pathway is defined by a space between a valve cover and a surface adjacent to the first and second chambers.

7. The device of claim 1 wherein the sealing means is comprised of a diaphragm located within the first fluid pathway.

8. The device of claim 6 wherein the sealing means is comprised of a diaphragm located within the first fluid pathway.

9. The device of claim 1 wherein the biasing means is comprised of a compression-resisting spring compressing the diaphragm at it a first end and compressing an opposite location of the device at its second end.

10. The device of claim 9 wherein the biasing means is comprised of:

a pin having a first end and a second end, the first end in contact with the diaphragm;

the second end of the pin in contact with a pivotable airway door assembly at a first pivotable end of the airway door assembly, wherein the pin extends through a valve cover;

wherein the airway door assembly is further in contact with the spring at a first spring end, the spring further being in contact with an adjustable screw threaded through an aperture in the device at a second spring end.

11. The device of claim 10 wherein the pivotable airway door assembly is provided with a second pivotable end having a stud and head, wherein the head is dimensioned to seal an aperture in the second fluid pathway.

12. The device of claim 1 wherein the actuable means is a provided with a bleed orifice.

13. The device of claim 1 wherein the compression means is a piston.

14. The device of claim 1 wherein the compression means is movable with said second chamber in response to movement of an arm attached to the compression means with such movement in at least one direction causing compression therein.

15. The device of claim 1 wherein the compression means comprises a propellant canister coupled to the second chamber to provide a desired pressure therein.

* * * * *

UNITED STATES PATENT AND TRADEMARK OFFICE
CERTIFICATE OF CORRECTION

PATENT NO. : 6,328,035 B1
DATED : December 11, 2001
INVENTOR(S) : Wakefield et al.

It is certified that error appears in the above-identified patent and that said Letters Patent is hereby corrected as shown below:

Column 6,
Line 62, cancel the term "diaphragm" and replace it with the term -- seal means --.

Signed and Sealed this

Twenty-sixth Day of July, 2005

JON W. DUDAS
*Director of the United States Patent and Trademark Office*